(12) United States Patent
Zinn et al.

(10) Patent No.: US 7,846,139 B2
(45) Date of Patent: Dec. 7, 2010

(54) VENOUS ACCESS PORT ASSEMBLY AND METHODS OF ASSEMBLY AND USE

(75) Inventors: Kenneth M. Zinn, Westport, CT (US); Mark S. Fisher, Sellersville, PA (US); Kevin Sanford, Chalfont, PA (US); William Shaun Wall, North Wales, PA (US); Raymond Bizup, Feasterville, PA (US); Timothy M. Schweikert, Levittown, PA (US)

(73) Assignees: Medical Components, Inc., Harleysville, PA (US); Innovative Medical Devices, LLC., Westport, CT (US)

( * ) Notice: Subject to any disclaimer, the term of this patent is extended or adjusted under 35 U.S.C. 154(b) by 359 days.

(21) Appl. No.: 11/724,945

(22) Filed: Mar. 16, 2007

(65) Prior Publication Data

US 2007/0219510 A1      Sep. 20, 2007

Related U.S. Application Data

(60) Provisional application No. 60/784,000, filed on Mar. 20, 2006.

(51) Int. Cl.
*A61M 37/00* (2006.01)
(52) U.S. Cl. .................................. 604/288.03
(58) Field of Classification Search ............. 604/288.03
See application file for complete search history.

(56) References Cited

U.S. PATENT DOCUMENTS 4,704,103 A   11/1987  Stober et al.
4,762,517 A   8/1988   McIntyre et al.
4,778,452 A   10/1988  Moden et al.

(Continued)

FOREIGN PATENT DOCUMENTS

WO        94/05351 A      3/1994

(Continued)

OTHER PUBLICATIONS

International Search Report, dated Dec. 18, 2007; PCT/US07/06689 (3 pages).

(Continued)

*Primary Examiner*—Nicholas D Lucchesi
*Assistant Examiner*—Jason Flick
(74) *Attorney, Agent, or Firm*—Blank Rome LLP

(57) ABSTRACT

An implantable venous access port for a catheter. The port assembly (100) includes a body (102), a septum (134) for needle insertion, a discharge port (150) having a passageway (154) and to which a catheter proximal end (202) is connected, and a proximal port (170) with a proximal passageway (172,116) that is in line with the discharge port passageway (154). A chamber (118) of the port body (102) fluidly connects the proximal port passageway and the discharge port passageway, and a proximal septum (174) traverses and seals the proximal passageway (172,116). An entry cannula (190) is insertable into the proximal opening and penetrates the proximal septum (174) and extends to the discharge port passageway (154) enabling a guide wire (198) to be inserted therethrough after the port (100) has been connected to the catheter (200), whereafter the entire assembly is implantable into a patient over the guide wire. A method of over-the-wire venous port placement is disclosed, and also a method for assembling the port.

25 Claims, 7 Drawing Sheets

U.S. PATENT DOCUMENTS

| | | | |
|---|---|---|---|
| 4,781,680 A | 11/1988 | Redmond et al. | |
| 4,915,690 A | 4/1990 | Cone et al. | |
| 5,108,377 A | 4/1992 | Cone et al. | |
| 5,180,365 A | 1/1993 | Ensminger et al. | |
| 5,185,003 A | 2/1993 | Brethauer | |
| 5,207,644 A | 5/1993 | Strecker | |
| 5,213,574 A | 5/1993 | Tucker | |
| 5,263,930 A | 11/1993 | Ensminger | |
| 5,281,199 A | 1/1994 | Ensminger et al. | |
| 5,356,381 A | 10/1994 | Ensminger et al. | |
| 5,360,407 A | 11/1994 | Leonard | |
| 5,399,168 A * | 3/1995 | Wadsworth et al. | 604/175 |
| 5,607,393 A | 3/1997 | Ensminger et al. | |
| 5,637,102 A | 6/1997 | Tolkoff et al. | |
| 5,713,858 A | 2/1998 | Heruth et al. | |
| 6,113,572 A | 9/2000 | Gailey et al. | |
| 6,190,352 B1 * | 2/2001 | Haarala et al. | 604/93.01 |
| 6,213,973 B1 | 4/2001 | Eliasen et al. | |
| 7,186,236 B2 | 3/2007 | Gibson et al. | |
| 2005/0085778 A1 | 4/2005 | Parks | |
| 2005/0171502 A1 * | 8/2005 | Daly et al. | 604/502 |
| 2006/0184142 A1 | 8/2006 | Schon et al. | |

FOREIGN PATENT DOCUMENTS

WO      WO 97/01370      1/1997

OTHER PUBLICATIONS

Written opinion, dated Dec. 18, 2007; PCT/US07/06689 (4 pages).
International Preliminary Examination Report, dated Jan. 12, 2009; PCT/US2007/06689 (9 pages).
European Search Report dated Jun. 5, 2009; EP 07753324.8 (12 pages).

* cited by examiner

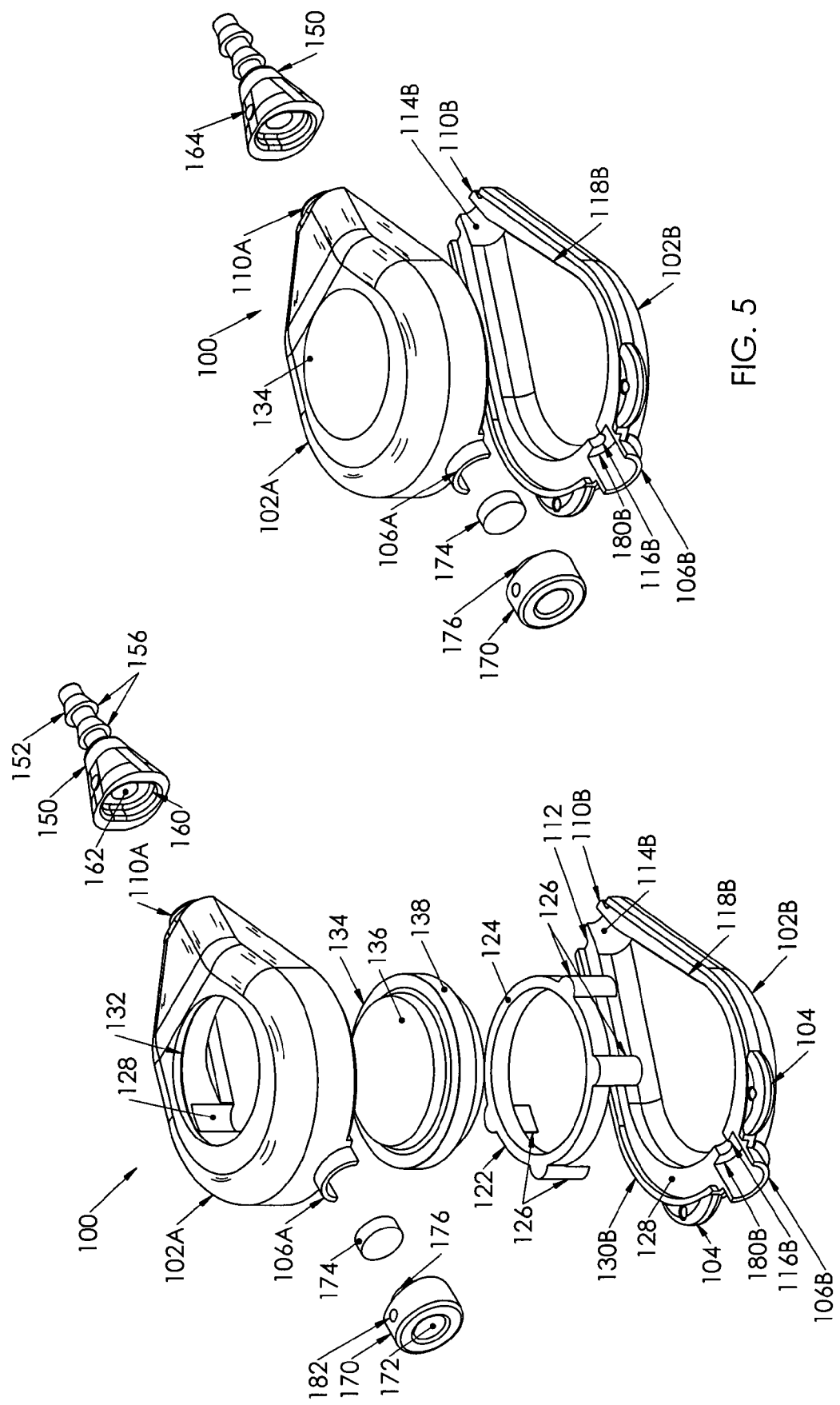

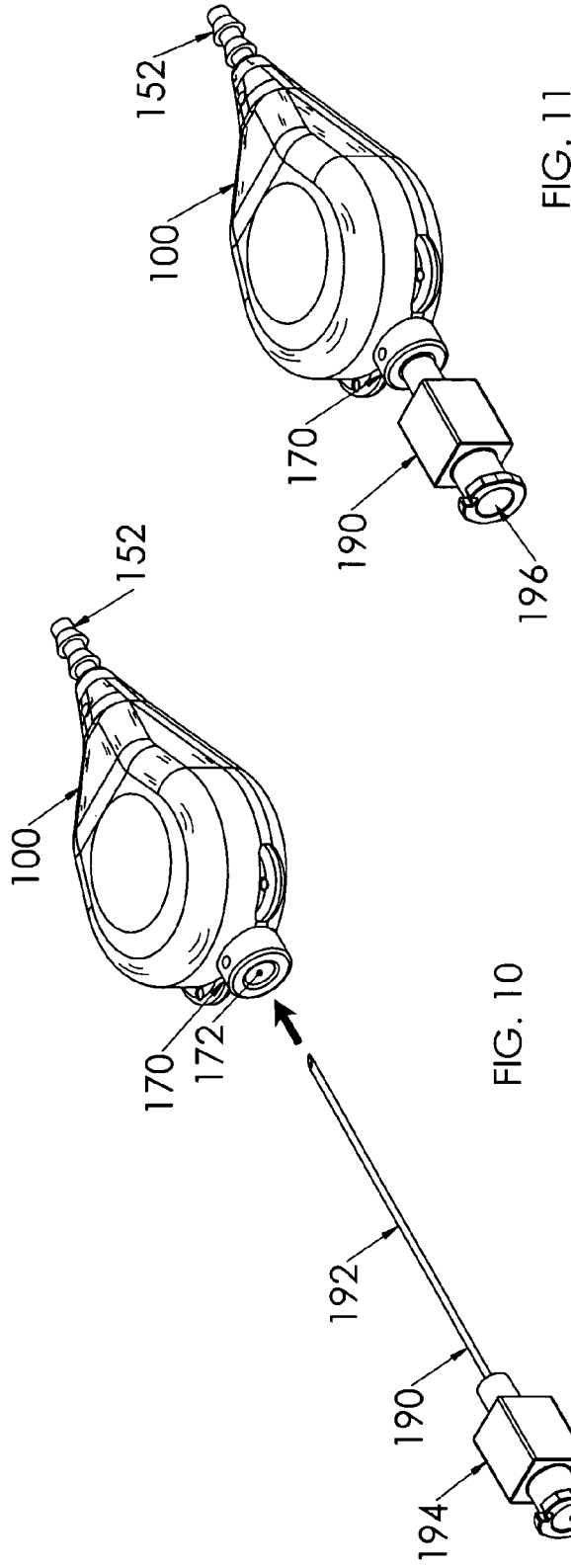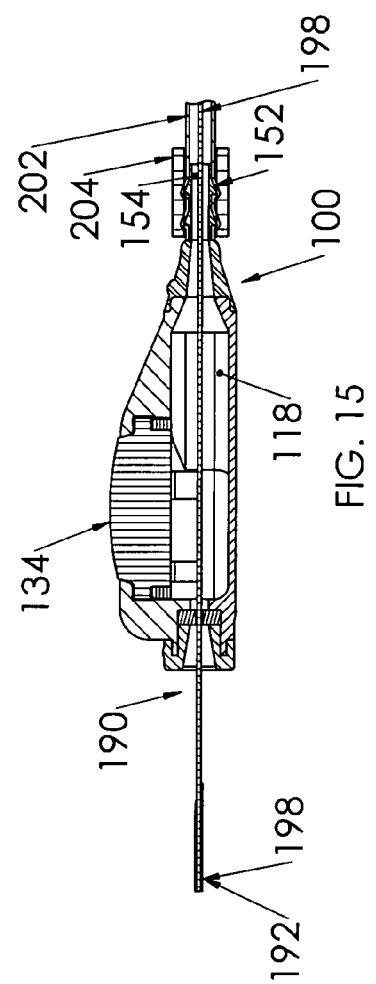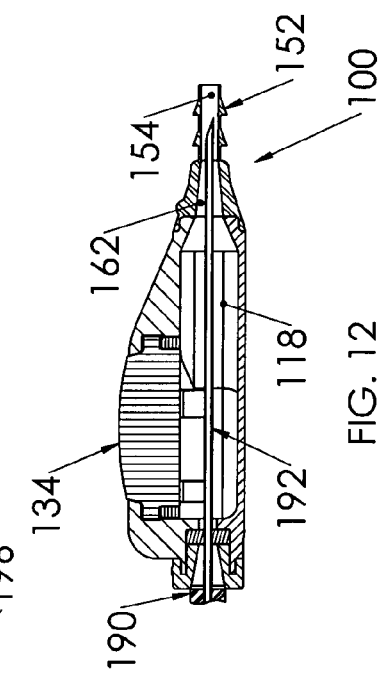

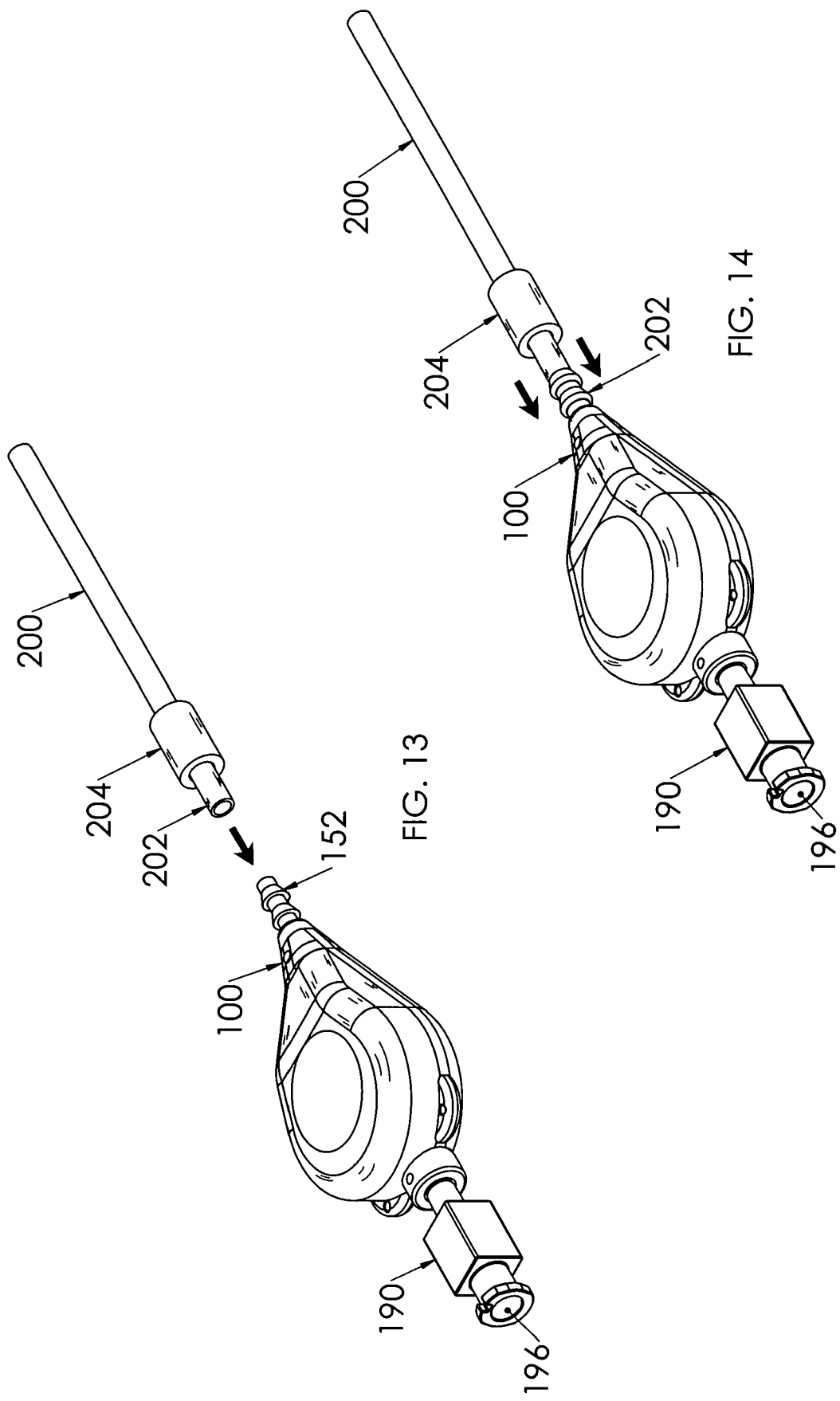

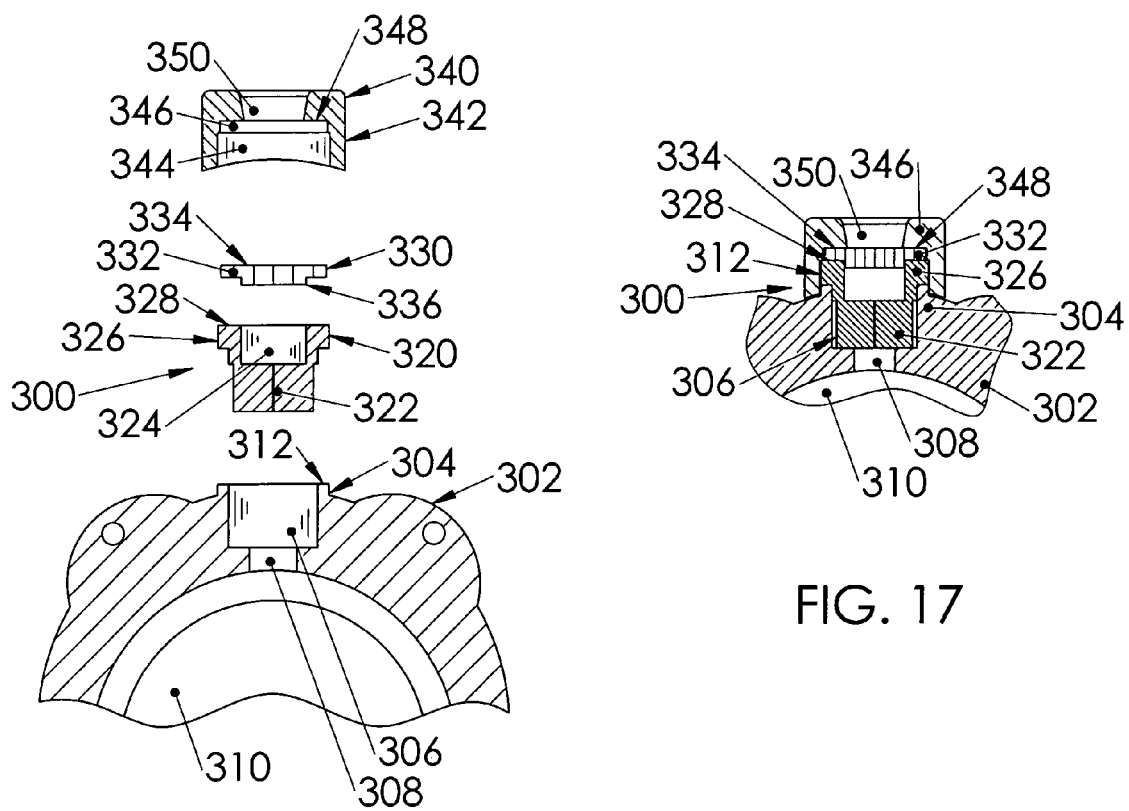
FIG. 16
FIG. 17
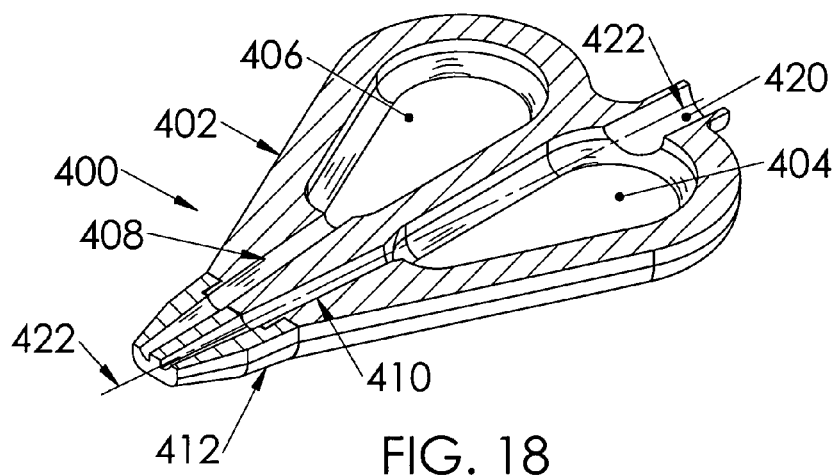
FIG. 18

VENOUS ACCESS PORT ASSEMBLY AND METHODS OF ASSEMBLY AND USE

CROSS-REFERENCE TO RELATED APPLICATION

This application claims priority from U.S. Provisional Patent Application Ser. No. 60/784,000 filed Mar. 20, 2006.

FIELD OF THE INVENTION

The present invention relates to medical devices and more particularly to venous access ports for catheters.

BACKGROUND OF THE INVENTION

Venous access ports for the infusion and/or withdrawal of fluids from a patient are well-known. These devices are typically used for drug infusion or small amounts of blood aspiration. Where large flows of fluid are required, larger ports can be used such as for hemodialysis or plasmapheresis.

Some ports may be implanted subcutaneously. Implantable venous access ports have the advantage that they can remain within the patient for prolonged periods of time, permitting multiple use and decreasing the risk for associated infection. These ports typically provide a septum defining an access site for multiple needle sticks without the need to continuously search for new access sites, since the septum is comprised of material such as silicone elastomer that self-seals each time as a needle is withdrawn. These ports also each include a stem, or discharge port, that extends through a distal wall and that has a passageway therethrough; the stem is secured to the proximal end of a catheter so that the discharge port passageway is in fluid communication with the catheter lumen. One such catheter infusion port is disclosed in U.S. Patent Publication No. US 2006/0184142 published on Aug. 17, 2006 (U.S. Ser. No. 11/335,369 filed Jan. 19, 2006). Another port is disclosed in U.S. Pat. No. 6,113,572.

Other types of ports are in use, known as dual ports or multi-ports. These provide two or more septa and internal chambers, all corresponding to different lumens of the attached catheter via respective separate discharge ports or alternatively, separate passageways in a single stem for communication with separate lumens of a dual or multi-lumen catheter, such as in U.S. Pat. No. 5,360,407.

Inherent in the placement of the presently commercially available implantable venous access ports is the risk of improper positioning. This can occur secondarily to the manipulation of the port and the attached catheter during placement into the subcutaneous port pocket. Catheter kinking or redundancy can occur. Furthermore, the catheter may be inadvertently withdrawn into a suboptimal intravenous location. These issues can lead to port failure necessitating readjustment during the procedure, or even replacement if failure is detected after implantation.

It would be most advantageous to provide a port that can be safely, easily and expeditiously inserted into the patient. Also, it would be an added benefit to be able to remove, positionally readjust and/or replace said port without undue difficulty, significantly prolonged procedure time or added risk to the patient.

BRIEF SUMMARY OF THE INVENTION

The present invention is an implantable venous access port for a catheter, that can be implanted into a patient over a guide wire. The port body includes at least one chamber accessible by a respective septum for needle insertion and withdrawal that self-seals, a discharge port to which a catheter proximal end is connected, and a proximal opening or port with a closure member or closure arrangement such as a septum or seal and/or a valve that is in line with the discharge port passageway.

In one embodiment, the port body of the present invention includes a single chamber, and a proximal port opening opens into the one chamber and is aligned with the passageway at the distal end of the venous access port that extends through the discharge port or stem for fluid communication with a catheter lumen.

In another embodiment, the port body can include dual chambers, each with a respective distal passageway through the discharge stem of the housing. The proximal port passageway is aligned with the distal passageway of one of the two chambers so that the guide wire will extend through that chamber from the proximal port to the discharge stem, to be disposed in a respective one of the dual lumens of the associated catheter.

An entry cannula is preferably utilized to facilitate insertion of the guide wire through the venous access port assembly. The entry cannula is insertable into the proximal opening and extends through the chamber (or one of a plurality thereof) into the discharge port passageway enabling a guide wire to be inserted therethrough after the port has been connected to the catheter, whereafter the entire assembly is implantable into a patient over the guide wire.

The present invention also provides a method for implanting a venous access port, comprising the steps of providing an implantable port with a discharge port for catheter connection, and a proximal opening in line therewith; connecting the port to the catheter proximal end; inserting a guide wire through the assembly and the catheter; and implanting the catheter and implantable venous access port over the guide wire.

Further, the present invention comprises a method of assembling a venous access port, in which the distal cap and proximal cap provide for securing together upper and lower port body portions, in cooperation with mating upper and lower distal and proximal semicylindrical flanges of the upper and lower body portions that together form circular distal and proximal flanges which are received into openings of the distal and proximal caps, respectively.

The present invention also comprises a venous access port assembly having a needle-impenetrable housing having upper and lower housing portions and defining an interior chamber, a needle-penetrable self-sealing septum traversing the chamber and a septum support that is at least independent of the upper housing portion and at least supported by the lower housing portion, wherein a peripheral top portion of the support supportably engages the inwardly facing peripheral surface of the septum, such that the upper housing portion when affixed to the lower housing portion, compresses a peripheral flange of the septum against the peripheral top portion of the support, retaining the septum assuredly in the housing.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIGS. 4 and 5 are fully exploded and partially assembled views of the port of FIGS. 1 to 3;

FIGS. 10 and 11 are isometric views of the port of FIGS. 1 to 9 showing an entry cannula;

FIG. 12 is a cross-sectional view showing the entry cannula of FIGS. 10 and 11 inserted into the port;

FIGS. 13 and 14 are isometric views of a catheter proximal end about to be assembled to the port of FIGS. 1 to 12 (FIG. 13), and fully assembled thereto (FIG. 14);

FIG. 15 is a cross-sectional view of the assembled port of FIG. 14 which also shows a guide wire inserted therethrough;

FIGS. 16 and 17 are enlarged sectional views of a second embodiment of proximal port closure arrangement shown exploded and assembled, respectively; and FIG. 18 is a cross-sectional view of a dual chamber port housing embodiment for being implanted over a guide wire.

DETAILED DESCRIPTION OF THE INVENTION

Figure 1:
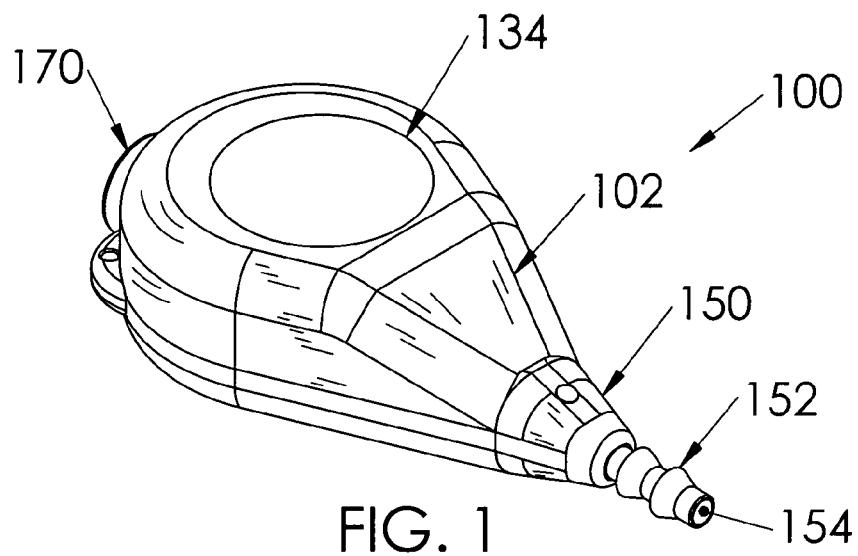
FIGS. 1 and 2 are isometric views from forward and rearward of the implantable port of the present invention.
Figure 2:
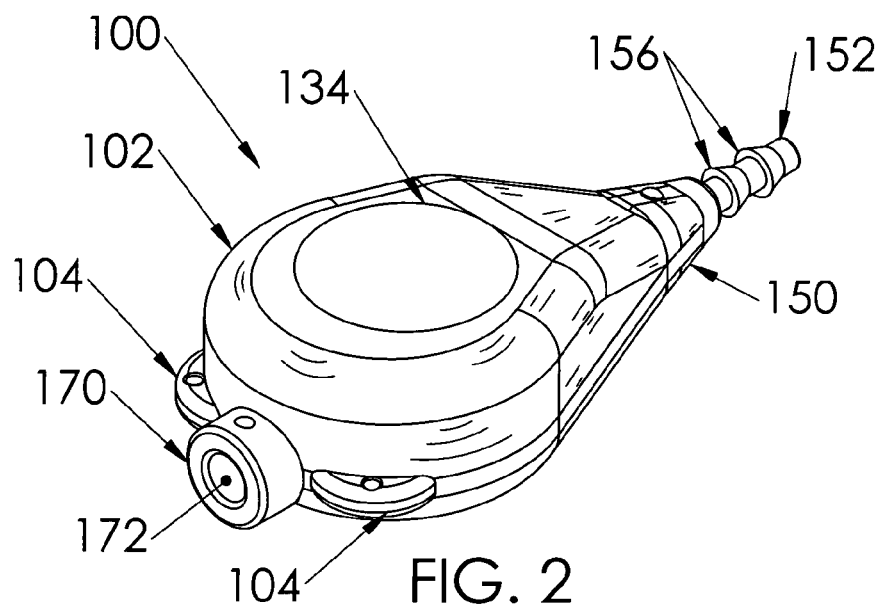
Figure 3:
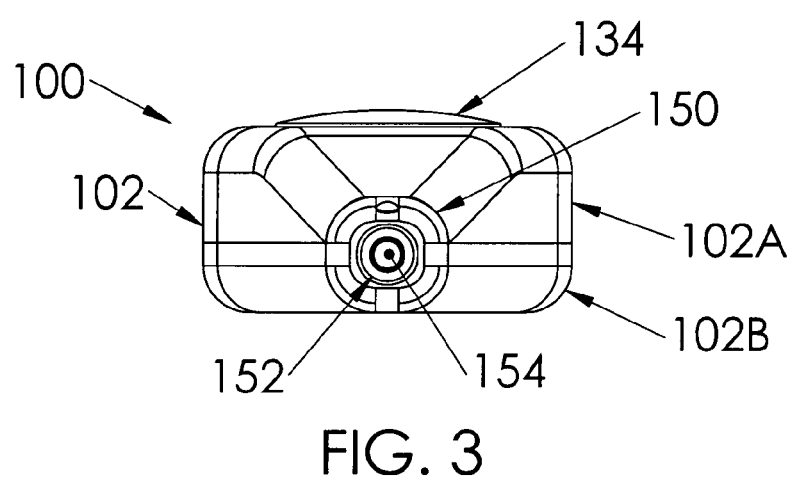
FIG. 3 is a front elevation view of the port of FIGS. 1 and 2.

In the drawings, like numerals indicate like elements throughout. Certain terminology is used herein for convenience only and is not to be taken as a limitation on the present invention. The terms "distal" and "proximal" refer, respectively, to directions closer to and away from the insertion tip of a catheter in an implantable catheter assembly. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

A first embodiment of the catheter port assembly of the present invention is illustrated in FIGS. 1 to 9. Port assembly 100 includes a body or housing 102 with a septum 134 exposed along the top of the port body and traversing the ceiling of a respective interior chamber 118, a discharge port 152 at the distal end of the port body, and a proximal port onto which is assembled a proximal cap 170. Discharge port 152 includes a passageway 154, and proximal cap 170 includes a proximal opening 172 that extends to an opening 116 at the proximal end of the port body 102. Port body 102 is comprised of an upper portion 102A and a lower portion 102B that are adhered or fused together along a horizontal parting line. The port assembly 100 also is shown to include a pair of suture wings 104 for securing the port assembly to the patient after implantation. Discharge port 152 is a distal section of distal cap 150 that is secured onto the distal end of port body 102, and is shown to include, preferably, annular rings or barbs 156 to secure the proximal end of a catheter to the port assembly (see FIGS. 13 and 14).

In FIGS. 4 and 5, the various parts of the port assembly 100 are shown exploded apart in FIG. 4, and partially assembled in FIG. 5. Upper and lower port body portions 102A,102B are shown to include semicylindrical distal flanges 110A,110B that upon assembly will comprise a circular distal flange 112 onto which distal cap 150 is securable. Similarly, upper and lower portions 102A,102B also include semicylindrical proximal flanges 106A,106B respectively, that upon assembly will comprise a circular proximal flange 108 onto which proximal cap 170 is securable. Also, in relation to proximal cap 170 is shown a proximal port closure member or septum (or seal) 174 of biocompatible self-sealing material such as silicone elastomer, that is secured within circular proximal flange 108 by proximal cap 170 and traverses the proximal port passageway 172,116, and which will be explained hereinbelow in relation to FIGS. 10 to 13. Optionally, the port closure member 174 can include or comprise a valve, as discussed below with reference to FIGS. 16 and 17.

Still referring to FIGS. 4 and 5, a septum 134 of self-sealing material is secured within port body 102, providing a site 136 for needle injection into the port assembly 100 after implantation, with site 136 preferably comprising a domed protrusion from the top surface of port body 102. Septum 134 also includes a peripheral flange 138 that is secured beneath an annular flange 132 that defines a septum-receiving opening of port body 102 upon assembly, upward through which extends the domed protrusion of the septum 134. The domed septum, although subcutaneous after placement of the venous port in the patient, provides a recognizable, palpable structure that can be located by the physician, or qualified personnel, for insertion of a needle therethrough for infusion or for the aspiration of blood, into or from the chamber, respectively. A septum support member 122 is defined within port body 102 that supports septum 134 upon assembly; the support member is independent of the upper housing portion 102A and at least supported by the lower housing portion 102B. Support member 122 includes a ring-shaped or peripheral top section 124 depending from which are a plurality of supports or legs 126, numbering four in this embodiment. Peripheral top section 124 will support peripheral flange 138 of septum 134 in upper body portion 102A, while legs 126 will rest on surface 128 of lower portion 102B upon assembly; the ring provides a substantial central clearance for insertion of the needle therethrough and into the chamber. Legs 126 are seen as being convex outwardly and preferably will fit into corresponding concave recesses 128 of the interior surface of upper body portion 106A under annular flange 132. The septum support member may initially be a discrete component assembled within the upper and lower housing portions, but it may also be molded as an integral part of lower housing portion 102B, if desired.

Also seen in FIGS. 4 and 5, proximal cap 170 is shown to define a proximal opening 172 and a distally extending flange section 176 that will be inserted into circular proximal flange 108 of port body 102 defined by upper and lower proximal flanges 106A,106B. Distally extending flange section 176 engages and retains proximal septum 174 within circular proximal flange 108 upon assembly, securing it against support surfaces 180A,180B of upper and lower body portions 102A,102B. A smaller diameter proximal passageway 116 is defined by semicylindrical surfaces 116A,116B at circular proximal flange 108 that is aligned with tapered surfaces 114A,114B at the distal end of chamber 118 extending to tapered transition opening 162 to distal passageway 154 through discharge port 152 (see FIG. 8). Chamber 118 is formed by chamber portions 118A,118B of upper and lower body sections 102A,102B and defines a reservoir for fluid injected into port assembly 100 through septum 134 after implantation.

Figure 6:
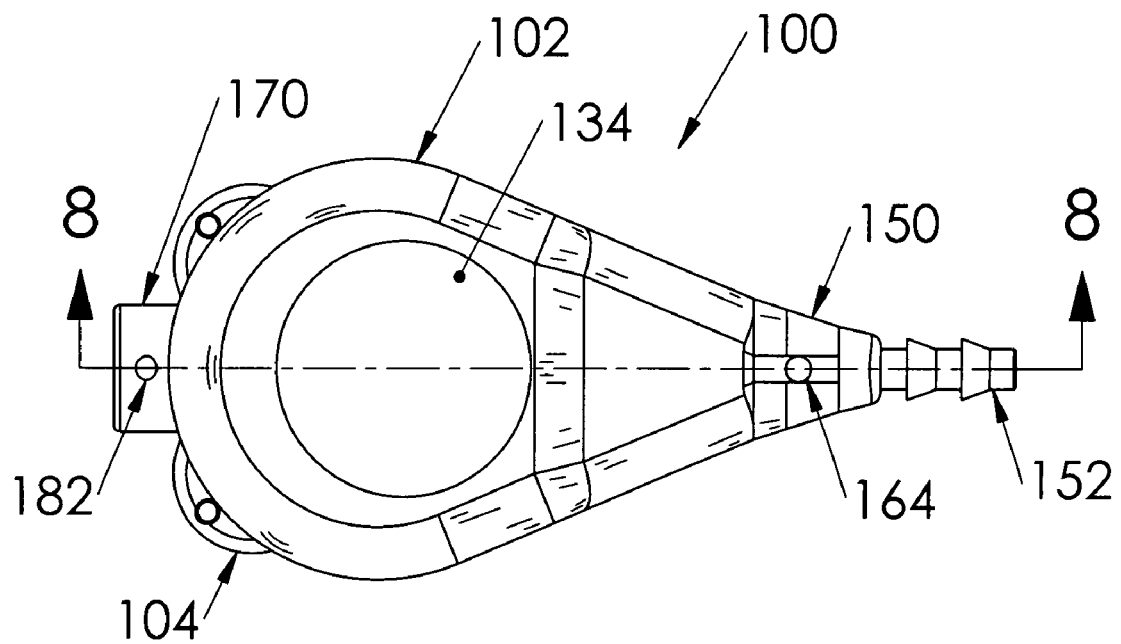
FIGS. 6 and 7 are top and side elevation views of the port of FIGS. 1 to 5.
Figure 7:
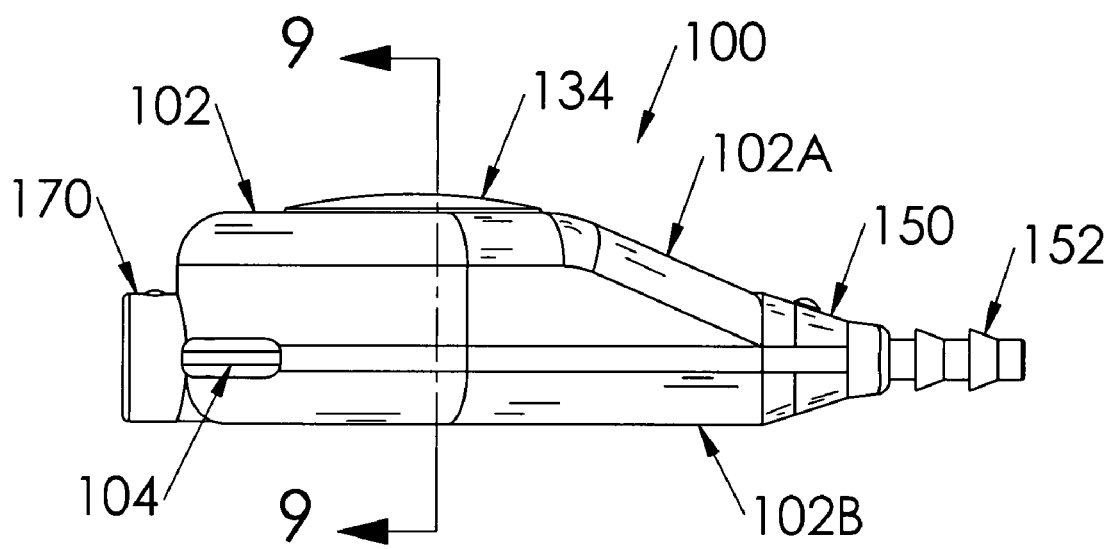
Figure 8:
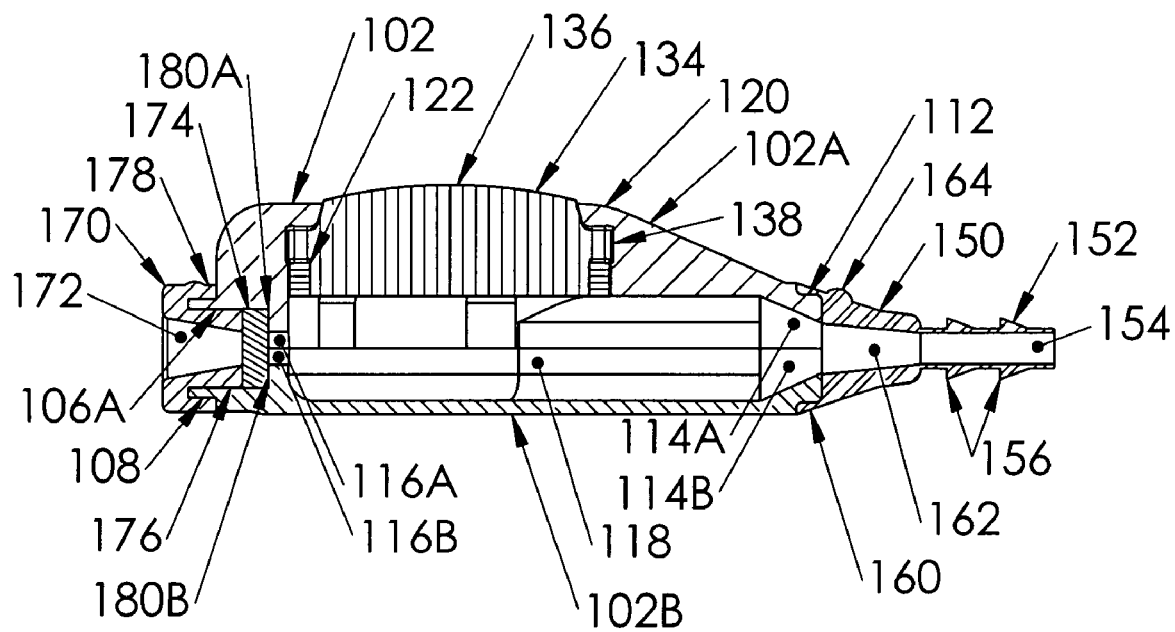
FIGS. 8 and 9 are cross-sectional views taken along lines 8-8 and 9-9 of FIGS. 6 and 7, respectively.
Figure 9:
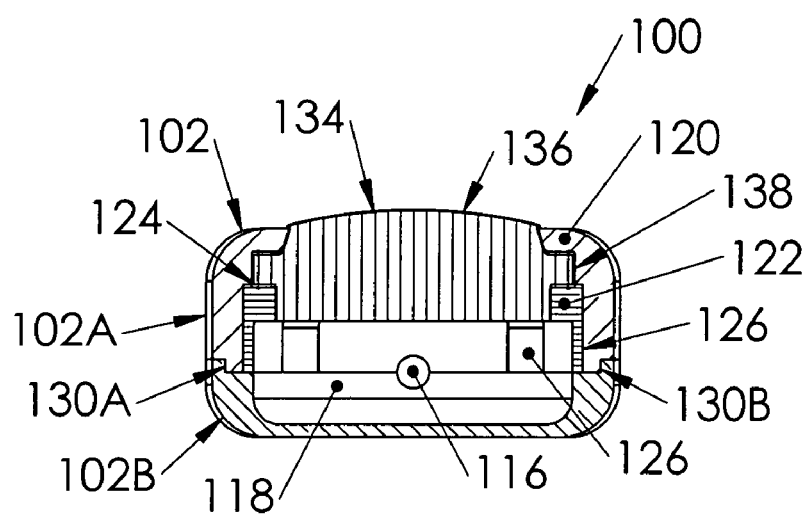

As seen in FIGS. 4, 5 and 9, septum 134 and septum support member 122 have been assembled into upper body portion 102A Upper and lower body portions 102A, 102B are now bonded together with outer peripheral ridge 130A of lower body portion 102A surrounding inner peripheral ridge 130B of upper body portion 102A, all surrounding surface 128 of lower body portion 102B. Distal semicylindrical flanges 110A,110B thus form circular distal flange 112, and proximal semicylindrical flanges 106A,106B thus form circular proximal flange 108. Distal cap 150 is now affixed to the distal end of port body 102, receiving circular distal flange 112 into large recess 160; circular distal flange 112 may be slightly undercut and the entrance periphery of large recess 160 may also be correspondingly undercut to define a snap fit, or they may have an interference fit, as well as being bonded and sealed. Proximal cap 170 is now affixed to the proximal end of port body 102, receiving proximal flange 108 around septum support section 176, again optionally in a force fit and being bonded and sealed, while securing septum 174 against surface 180 of port body 102. Together, it is seen that distal and proximal caps 150,170 mechanically assist in maintaining upper and lower body portions 102A,102B together, supplementing the bonding and sealing between the upper and lower body portions. To assist proper assembly, visual and tactile indicators 164 and 182 are shown provided on top surfaces of distal cap 150 and proximal cap 170 to indicate the appropriate vertical orientation for assembly to the circular distal and proximal flanges of the now-assembled upper and lower body portions of port body 102. Fully assembled port assembly 100 is shown in FIGS. 6 and 7, from which the cross-sectional views of FIGS. 8 and 9 are taken. The material for molding of the housing portions and cap is biocompatible and may be, for example, acetal, polysulfone, or ABS, or it may be titanium alloy, if desired.

Now referring to FIGS. 10 to 15, port assembly 100 is shown receiving entry cannula 190 into proximal opening 172 of proximal cap 170. Entry cannula 190 includes a distal cannula section 192 extending from body 194, which has a proximal opening 196 which is funnel-shaped to receive inserted thereinto a distal end of a guide wire (FIG. 15). Cannula section 192 is shown to extend through chamber 118 of port assembly 100 and through tapered transition opening 162 of distal cap 150, and into passageway 154 of discharge port 152.

In FIGS. 13 and 14, a proximal end 202 of a catheter 200 is shown being connected to discharge port 152 of port assembly 100. The proximal catheter end is force fit over the discharge port stem and over and past the retention barbs 156. A compression sleeve 204 is then moved proximally over proximal catheter end 202 to compress the catheter walls more firmly against the discharge port stem.

In FIG. 15, a guide wire 198 is shown having been inserted into entry cannula 190 and through cannula section 192 and chamber 118 and into discharge port passageway 154 and into the proximal catheter end 202. The implantable port of the present invention is now implantable into a patient over a guide wire, along with the catheter to which the implantable port is firmly connected.

Another arrangement of the proximal port closure of the venous access port assembly of the present invention is seen in FIGS. 16 and 17. Arrangement 300 is shown to have a valve 320, a septum 330 and a cap 340, all associated with proximal port 306 of housing 302. A proximal flange 304 protrudes proximally from the housing to a transverse surface 312. Valve 320 includes a valve portion 322 that is closed but is slit to permit an entry cannula (FIG. 10) to pass therethrough during implantation. Valve 320 further includes a proximal recess 324 proximally of the valve portion 322, extending to a widened collar 326 defining a transverse proximal surface 328. Septum 330 is imperforate of self-sealing material and is preferably disc-shaped with a distal protrusion to fit partially into the proximal recess 324 of valve 320, and has an annular collar 332, and defines a transverse proximal surface 334. Valve 320 may for example be made of a biocompatible material such as silicone elastomer. Septum 330 may for example also be made of silicone elastomer, similar to septum 174 of FIG. 4.

Cap 340 of FIGS. 16 and 17 is seen to have a cylindrical distal portion 342 with a recess 344 to receive thereinto the widened collar 326 of valve 320; a septum seat 346 into which is received annular collar 332 of septum 330; and a narrowed portion defining a distally facing compression surface 348, and a proximal opening 350 preferably chamfered to define a lead-in for insertion thereinto of the distal tip of an entry cannula (FIG. 10) which eventually enters chamber 310 by opening 308. Cap 340 is assembled and bonded to the proximal flange 304 of housing 302, and by compression surface 348, compresses septum 330 against the proximal surface 328 of valve 320 thus compressing the widened valve collar 326 against the transverse surface 312 of the proximal port of the housing while compressing the valve material radially outwardly against the interior surfaces of at least the cap at recess 344 and sealing the proximal port of the port housing. Cap 340 may be made for example of polysulfone, similar to cap 170 of FIG. 4.

The method of the present invention is discerned in the Figures and the above discussion by assembling the port assembly; inserting the entry cannula; connecting the port assembly to a catheter proximal end; inserting a guide wire through the entry cannula, the port assembly and the catheter; and implanting the catheter/port assembly into a patient over the guide wire.

Other embodiments of the over-the-wire venous access port assembly of the present invention can include at least two interior chambers with respective septa, each extending to a respective discrete passageway through the discharge stem for fluid communication with a respective lumen of a multi-lumen catheter secured onto the discharge stem. One of the chambers can include a portion in-line between the proximal port and the discharge stem for insertion therethrough of the guide wire, with or without the use of the entry cannula.

One such dual chamber port 400 is illustrated in FIG. 18. A cross-section of the base housing part 402 illustrates that the proximal port opening 420 is aligned with the distal passageway 408 of chamber 404, defining an axis 422, such that the guide wire (not shown) will extend from the proximal port to the distal passageway 408 of chamber 404 at the discharge port 412, through chamber 404, while the second chamber 406 is not involved and has its own associated distal passageway 410 at the discharge port 412.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A venous access port for use with a catheter that is to be inserted intravascularly in a patient, comprising:
  a port assembly having a body, at least one septum for infusion by needle, a discharge port for connection with a catheter proximal end and having at least one passageway therethrough, a proximal port having a passageway therethrough, at least one chamber with which the at least one septum is associated establishing fluid communication with a respective at least one discharge port passageway and with the proximal port passageway, and a proximal port closure traversing the proximal port passageway, the proximal port closure further comprising a proximal septum and a proximal valve, wherein the proximal port is in line with the discharge port enabling a guide wire to extend linearly through the at least one chamber from the proximal port, through the proximal port closure, through the at least one chamber and into and through the at least one passageway of the discharge port into the catheter, whereby the venous access port is adapted to be placed into a patient over the guide wire after connection of the catheter proximal end thereto and insertion of the guide wire therethrough.

2. The venous access port of claim 1, further including at least a second chamber.

3. The venous access port of claim 1, further including an entry cannula insertable into the proximal port and through the proximal port closure, through the at least one chamber and extending partially into the discharge port, facilitating insertion of a guide wire through the venous access port by being inserted into and through the entry cannula and into the at least one discharge port passageway and into the catheter proximal end.

4. The venous access port of claim 1, wherein the septum associated with the at least one chamber is disposed in an opening in the top of the body and includes a peripheral flange underlying a periphery of the body opening, and wherein the port assembly further includes a support member disposed within the port body spaced from the discharge port and openings extending to the discharge port and the proximal port from the chamber, the support member supporting the at least one septum.

5. The venous access port of claim 4, wherein the support member includes a peripheral top portion engageable at least with the peripheral flange of the septum, the peripheral top portion defining a clearance through which a needle is insertable through the septum into the at least one chamber.

6. The venous access port of claim 1, wherein the proximal port is generally aligned with each other and with the at least one discharge port passageway.

7. The access port of claim 1, wherein the valve comprising a valve portion that is slit to permit the entry cannula to pass therethrough.

8. The access port of claim 1, wherein the port body includes an upper body portion and a lower body portion that each partially defines portions of the openings from the chamber to both the at least one discharge port passageway and the proximal port closure, and that upon assembly to each other, together define the openings, the openings being generally aligned with each other and with the discharge port passageway.

9. The venous access port of claim 8, wherein the support member further includes supporting sections supportingly engageable with a support surface defined by the lower body portion.

10. The venous access port of claim 9, wherein the support surface peripherally surrounds the at least one chamber and is substantially sealingly joined to a complementary surface of the upper body portion upon assembly.

11. The venous access port of claim 10, wherein the upper body portion includes a downwardly extending peripheral ridge cooperable with a complementary upwardly extending peripheral ridge of the lower body portion to enhance the joint between the upper and lower body portions upon assembly.

12. The venous access port of claim 11, wherein the upwardly extending peripheral ridge is outwardly of the downwardly extending peripheral ridge.

13. The venous access port of claim 8, wherein the upper body and the lower body portions define distally extending semicylindrical sections that together cooperate to define upon port assembly a circular distal flange.

14. The venous access port of claim 13, further including a distal cap affixable to and around the circular distal flange, and wherein the connection of the distal cap to the circular distal flange is a force fit.

15. The venous access port of claim 14, wherein the discharge port includes at least one annular protrusion circumferentially around an outer surface thereof, facilitating assured connection of a catheter proximal end therearound and thereto.

16. The venous access port of claim 15, wherein the at least one annular protrusion comprises an annular barb.

17. The venous access port of claim 15, wherein the discharge port includes a plurality of the annular protrusions.

18. The venous access port of claim 8, wherein the upper body and the lower body portions define proximally extending semicylindrical sections that together cooperate to define upon port assembly a circular proximal flange.

19. The venous access port of claim 18, wherein the proximal port includes a proximal cap affixable to and around the circular proximal flange.

20. The venous access port of claim 19, wherein the proximal cap includes a distally extending annular flange that engages and supports the proximal port closure member, retaining the proximal port closure in the port assembly.

21. The venous access port as set forth in claim 8, wherein the upper body portion includes a downwardly extending peripheral ridge cooperable with a complementary upwardly extending peripheral ridge of the lower body portion to enhance the joint between the upper and lower housing portions upon assembly.

22. A venous access port for use with a catheter that is to be inserted intravascularly in a patient, comprising:
a port assembly having a body comprising upper and lower housing portions, at least one septum for infusion by needle, a discharge port for connection with a catheter proximal end and having at least one passageway therethrough, at least one chamber with which the at least one septum is associated establishing fluid communication with a respective at least one discharge port passageway, and a septum support independent of the upper and lower housing portion and at least supported by the lower housing portion, spaced from the discharge port and an opening extending thereto from the chamber, the septum support having peripheral top portion in compressive support with a peripheral flange of the septum upon assembly of the port, and a plurality of supports.

23. The venous access port as set forth in claim 22, wherein the septum support member further includes supporting sections at least supportingly engageable with a support surface defined by the lower housing portion.

24. The venous access port as set forth in claim 23, wherein the support surface peripherally surrounds the at least one chamber and is substantially sealingly joined to a complementary surface of the upper housing portion upon assembly.

25. A venous access port for use with a catheter that is to be inserted intravascularly in a patient, comprising:
a port assembly having a body, at least one septum for infusion by needle, a discharge port for connection with a catheter proximal end and having at least one passageway therethrough, a proximal port having a passageway therethrough, at least one chamber with which the at least one septum is associated establishing fluid communication with a respective at least one discharge port passageway and with the proximal port passageway, and a proximal port closure traversing the proximal port passageway, and an entry cannula insertable into the proximal port and through the proximal port closure, through the at least one chamber and extending partially into the discharge port, facilitating insertion of a guide wire through the venous access port by being inserted into and through the entry cannula and into the at least one discharge port passageway and into the catheter proximal end, wherein the proximal port is in line with the discharge port enabling a guide wire to extend linearly through the at least one chamber from the proximal port, through the proximal port closure, through the at least one chamber and into and through the at least one passageway of the discharge port into the catheter, whereby the venous access port is adapted to be placed into a patient over the guide wire after connection of the catheter proximal end thereto and insertion of the guide wire therethrough.

* * * * *